United States Patent [19]

Petersen

[11] Patent Number: 4,710,350

[45] Date of Patent: Dec. 1, 1987

[54] APPARATUS AND METHOD FOR STERILIZING WITH VAPORIZABLE LIQUIDS

[76] Inventor: C. William Petersen, 295 Poplar, Elmhurst, Ill. 60126

[21] Appl. No.: 851,313

[22] Filed: Apr. 9, 1986

Related U.S. Application Data

[63] Continuation of Ser. No. 625,319, Jun. 27, 1984, abandoned.

[51] Int. Cl.$^4$ .............................................. A61L 2/20
[52] U.S. Cl. ........................................ 422/37; 422/107; 422/109; 422/295; 422/298; 55/385 C; 219/272
[58] Field of Search ................. 422/37, 105, 107–111, 422/292–300, 307; 219/271, 272, 275, 276; 55/385 C; 220/371

[56] References Cited

U.S. PATENT DOCUMENTS

| | | | |
|---|---|---|---|
| 717,448 | 12/1902 | Tucker | 422/298 |
| 2,722,593 | 11/1955 | McAlister | 219/272 |
| 3,411,866 | 11/1968 | Jewell | 422/109 |
| 3,579,290 | 5/1971 | Pickstone . | |
| 3,944,387 | 3/1976 | Schreckendgust | 422/295 |
| 4,194,950 | 3/1980 | Zalles | 202/185.1 |
| 4,259,293 | 3/1981 | Najarian et al. | 422/109 |
| 4,263,258 | 4/1981 | Kalasek | 422/298 |

OTHER PUBLICATIONS

M. Klein et al., Rapid Sterilization by Heat Using Fluorocarbon Vapour As The Heat Transfer Medium, Excerpted Medica International Congress Series No. 222, Ophthalmology, Proceeding of the XXI International Congress, Mexico, D.F. 8-14, Mar. 1970, pp. 1501-1505.

Primary Examiner—David L. Lacey
Attorney, Agent, or Firm—Glenn A. Busé

[57] ABSTRACT

A sterilizing device includes a heating chamber having a reservoir containing a substantially inert, vaporizable liquid having a boiling point sufficiently high to kill microorganisms unsafe for humans. The sterilizing liquid is heated to boiling by a heater submerged therein. The articles to be sterilized are placed in a perforated tray located in the chamber above the reservoir and are contacted by a blanket of substantially saturated vapors of the sterilizing liquid. A temperature controller turns the heater off and on in response to the vapor blanket rising to and falling below a predetermined level above the tray. A counter counting the number of electrical impulses or cycles thereafter transmitted to the heater turns off the heater after a predetermined number of such cycles and a fan or similar cooling apparatus is energized to cool the chamber and condense the vapors. Vapors entrained in the air displaced from the chamber by the rising vapor blanket are either removed by a filter arrangement or collected along with the air in an inflatable member and returned to the chamber after completion of the sterilizing cycle.

12 Claims, 6 Drawing Figures

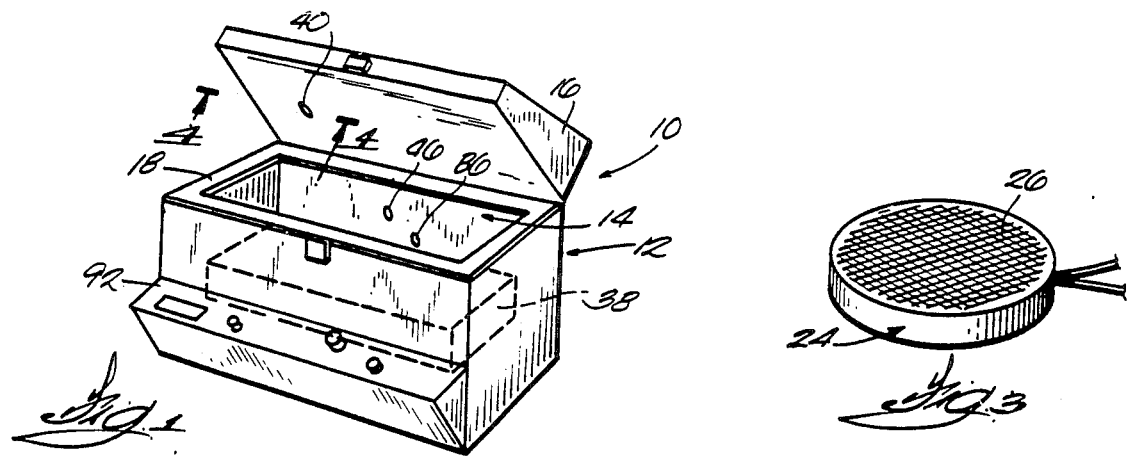
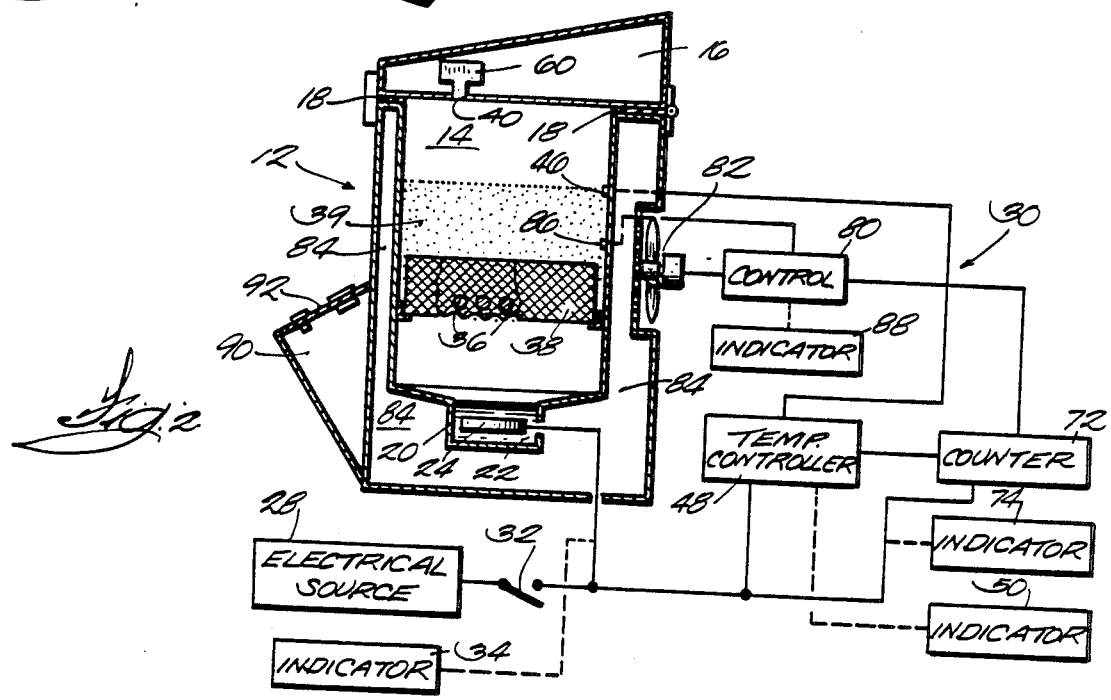
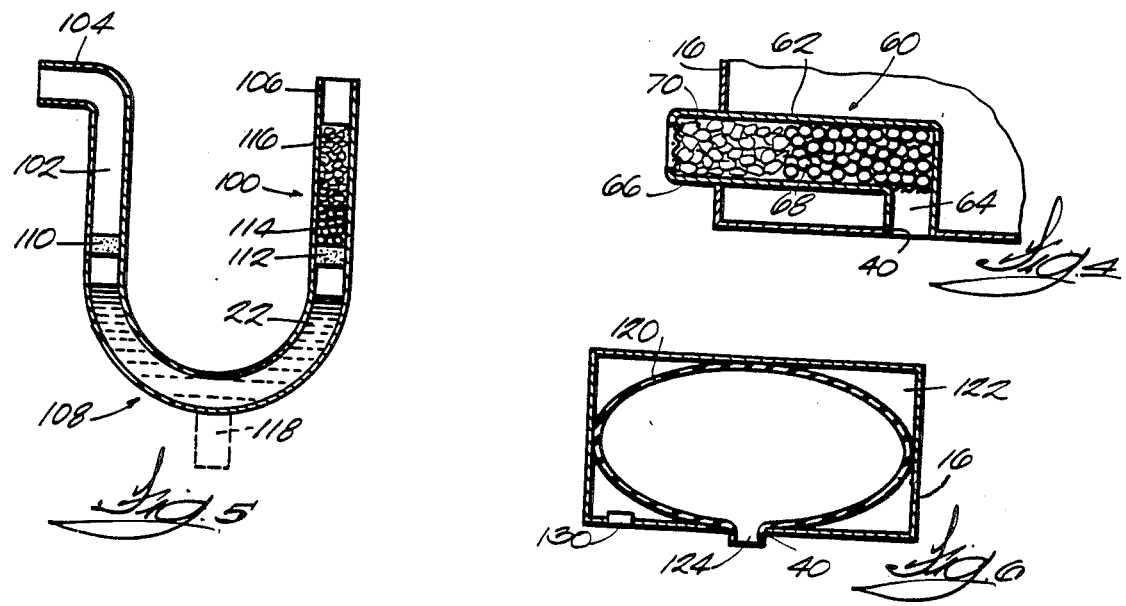

APPARATUS AND METHOD FOR STERILIZING WITH VAPORIZABLE LIQUIDS

CROSS REFERENCE TO RELATED APPLICATION

This application is a continuation of application Ser. No. 625,319, filed June 27, 1984, now abandoned.

BACKGROUND OF THE INVENTION

This invention relates to sterilization of articles, such as surgical instruments, dental instruments and the like, and, more particularly, to sterilization devices and methods employing fluorocarbon liquids as the sterilization medium.

Sterilization of surgical instruments, dental instruments and the like to destroy a wide variety of microorganisms is mandatory in the health science and service fields. Various sterilization techniques have been employed, including exposing the articles to chemical vapors, such as ethylene oxide, to X-ray radiation, to wet heat and to dry heat. The two most widely used techniques are wet heat by pressurized, saturated steam in an autoclave or the like and dry heat in some form of oven.

Steam autoclave sterilizers are quite bulky and expensive, usually require the use of distilled water, and the steam can cause corrosion (unless a corrosion inhibitor is used) and dulling of cutting edges. Hot air oven sterilizers generally are quite slow in reaching the elevated temperatures required for sterilization, require prior thorough cleaning and drying of the articles to be sterilized to remove any material which may insulate underlying microorganisms or become baked on the surface and, when several articles are to be sterilized at once, require special packaging and/or placement of the articles in the oven to insure uniform sterilization of all the articles.

The use of fluorocarbon liquids for sterilization is disclosed in an article by M. Klein and D. G. Millwood entitled "Rapid Sterilization by Heat Using a Fluorocarbon Vapour as the Heat Transfer Medium", reprinted from Excerpted Medica Interantional Congress Series No. 222, OPHTHALMOLOGY, Proceedings of the XXI International Congress, Mexico, D. F. 8–14 Mar. 1970. Such liquids are substantially chemically and biologically inert, non-flamable, thermally stable and have boiling points at temperatures above that required for sterilization. The liquid is heated to boiling and the vapors are allowed to contact and rapidly heat the articles to be sterilized.

Various sterilization devices employing fluorocarbon liquids as the sterilizing medium have been proposed. For example, Pickstone U.S. Pat. No. 3,579,290 discloses a device in which a fluorocarbon liquid located in the lower portion of a chamber is heated to boiling and surgical instruments or the like are lowered into the vapors above the liquid for sterilization. Najarian et al U.S. Pat. No. 4,259,293 discloses a device including a pressurized heating chamber in which the vapors from a boiling fluorocarbon liquid pass over surgical instruments to be sterilized and a relatively complicated system for recovering vapors expelled from the chamber including several valves for condensing vapors, collecting the condensed vapors and returning the collected liquid to the heating chamber. These devices are quite bulky and require a number of moving parts.

SUMMARY OF THE INVENTION

An object of the invention is to provide a simply constructed, convenient-to-operate, sterilizing device which is adapted to use substantially inert, odorless and nonflamable liquids, such as fluorocarbon liquids, as the sterilizing medium.

Another object of this invention is to provide such a sterilizing device which can be operated with a minimum loss of the sterilizing medium and yet does not include a complicated vapor recovery system.

A further object of the invention is to provide such a sterilizing device including means for controlling vaporization of the sterilizing medium in a manner to insure adequate sterilization irrespective of the number of items being sterilized.

A yet further object of the invention is to provide a simplified method for sterilizing articles, such as surgical instruments, dental instruments and the like, which employs fluorocarbon liquids and does not require movement of the articles during the sterilization cycle or the use of complicated vapor recovery systems.

Other objects, aspects and advantages of the invention will become apparent to those skilled in the art upon reviewing the following detailed description, the drawings, and the appended claims.

The invention provides a sterilizing device including a housing defining an interior chamber, a reservoir in the lower portion of the chamber for containing a substantially non-toxic, substantially inert, vaporizable sterilizing liquid having a boiling point sufficiently high to kill microorganisms unsafe for humans, an electrical heater for heating and vaporizing the sterilizing liquid, a support located above the reservoir for supporting articles to be sterilized and permitting rising vapors to contact and pass over the articles, and an electrical control circuit adapted to be connected to a source of electrical energy for controlling the operation of the heater and thereby control the level of the vapors in the chamber. The control circuit includes a sensor located above the support for sensing the presence of a relatively dense vapor blanket and is operable to permit the flow of electrical energy to the heater in response to the sensor sensing the absence of a vapor blanket and to terminate the flow of electrical energy to the heater after a predetermined period sufficient to sterilize the articles subsequent to the sensor sensing the presence of a vapor blanket.

In one embodiment, the sterilizing liquid is a fluorocarbon liquid having a boiling point of at least about 100° C., preferably at least about 150° C.

In one embodiment, the device includes means for recovering vapors of the sterilizing liquid entrained in the air displaced from the chamber.

In one embodiment, the heater is submerged in the sterilizing liquid and includes a heating element made from a positive temperature coefficient material which produces a substantially constant surface temperature.

In one embodiment, the control circuit includes a a counting means for counting the number of electrical (hertz) cycles transmitted to the heater after it has been turned on and for terminating the sterilizing cycle after a predetermined number of electrical cycles.

In one embodiment, the device includes an electrically operated cooling means for cooling the chamber and the control means in response to termination of the sterilizing cycle.

BRIEF DESCRIPTION OF THE DRAWING

FIG. 1 is a perspective, partially schematic, view of a sterilizing device embodying the invention.

FIG. 2 is an enlarged side elevational view of the sterilizing device shown in FIG. 1 and a schematic representation of the electrical control circuit.

FIG. 3 is an enlarged perspective view of the heater in the sterilizing device shown in FIG. 1.

FIG. 4 is an enlarged schematic view of the vapor recovery means taken generally along line 4—4 in FIG. 1.

FIG. 5 is an enlarged schematic view of an alternate arrangement for the vapor recovery means.

FIG. 6 is an enlarged schematic view of another alternate arrangement for the vapor recovery means.

DESCRIPTION OF THE PREFERRED EMBODIMENTS

Illustrated in the drawings is a sterilizing device 10 for sterilizing surgical instruments, dental instruments and the like. The sterilizing device 10 has a housing 12 defining an interior chamber 14 and an access door or cover 16 which, when closed, engages a peripheral gasket 18 to form a seal for retaining vapor inside the chamber 14. If desired, a front access door can be used in place of cover 16.

A reservoir 20 containing a vaporizable, sterilizing liquid 22 is located in the bottom of the chamber 14. While the reservoir 20 is an integral part of the chamber 14 in the specific embodiment illustrated, it can be a separate, removable container.

The sterilizing liquid 22 is a substantially nontoxic, substantially inert, vaporizable liquid having a boiling point sufficiently high to destroy (i.e., disturb the protein nature) microorganisms unsafe for humans, particularly the hard-shelled spore *bacillus stearothermophilus*, within a relatively short time period in the order 0.5 to 30 minutes. Although not absolutely critical, the sterilizing liquid generally should have a boiling point of at least about 100° C., preferably at least about 150° C.

Fluorocarbon liquids having a completely fluorinated structure, i.e., no chlorine or hydrogen in the molecular configuration, are preferred because, in addition to having low toxicity and being biologically and chemically inert, they are colorless, odorless, non-flammable, thermally stable, non-polar and substantially dielectric. They also have a high density, low viscosity, low heat of vaporization and low surface tension and leave essentially no residue. Suitable commercially available fluorocarbon liquids include the "Fluorinert" liquids marketed by 3M Company, particularly FC-75, FC-40, FC-43 and FC-70 which have boiling points of 102°, 165°, 174°and 215° C., respectively.

The sterilizing liquid 22 is heated to boiling by a suitable heating means either submerged in the sterilizing liquid 22 or located in heat transfer relationship with the reservoir 20. In the specific construction illustrated, the heating means comprises an electric heater 24 submerged in the sterilizing liquid 22 and including a heating element 26 (FIG. 3) constructed from a positive temperature coeffecient (PTC) thermistor material. Such heaters can be made from a variety of materials such as barium titanate, beryllium oxide and the like and usually have a Curie point making them self-regulating without the need for a thermostat. Suitable commercially available PTC type heaters are marketed by TDK Corporation of America and also by GTE Sylvania Corporation under the "THERMASTER" trademark.

While the heating element can have various geometric configurations, it preferably has a honeycomb construction as shown in FIG. 3 or similar multi-surface construction to provide a high surface or heating area for rapidly bringing the sterilizing liquid 22 to its boiling point or vaporization level. Since fluorocarbon liquids generally have lower dielectric values, the electrical heating element 26 does not have to be insulated from the sterilizing liquid 22 by an electrically non-conductive material. Instead, it can be placed in direct contact with the sterilizing liquid 22 to maximize heat transfer efficiency and minimize the time required to bring the sterilizing liquid 22 to its boiling point. PTC thermistor type heaters are particularly suitable because they have a predetermined maximum temperature (Curie point) and will not overheat even though the level of the sterilizing liquid 22 might accidentally drop below the top surface of the heater 24.

The heater 24 is connected to a source of electrical energy 28 through an electrical control circuit 30 including a starter switch 32 which is movable between an "off" and an "on" position to energize the heater 24. The control circuit 30 also includes a light emitting diode (LED) 34 or similar indicating means which is illuminated any time the heater 24 is operating.

Articles to be sterilized, such as dental instruments 36, are supported above the reservoir 20 on a perforated shelf or in a removable perforated tray 38 as illustrated. The vapors 39 from the boiling sterilizing liquid 22 contact and pass over the instruments 36 as they rise toward the upper portion of the chamber 14. While only a single tray 38 is illustrated, two or more tiers of vertically spaced shelves or trays 38 can be used.

The vapors 39 of the sterilizing liquid 22 are more dense than air and substantially immiscible with air. Consequently, a relatively dense blanket of substantially saturated vapors is formed and displaces the air in the chamber 14 toward the upper portion. The displaced air expelled through a vent passage 40 in the cover 16 is either collected or discharged to the atmosphere as explained in more detail below. As the dense vapors contact the instruments 36, they condense and, because of the low surface tension of the sterilizing liquid, the condensate rapidly drains back into the reservoir 20. The condensate is rapidly replaced with hot vapors which contact the instruments 36, resulting in rapid heating.

Located above the uppermost tray 38 and any instruments 36 supported thereon is a sensing means for sensing the presence of a relatively dense blanket of the sterilizing liquid vapors 39. In the specific embodiment illustrated, the vapor sensing means comprises a temperature sensor 46 and a conventional temperature controller 48 which is set at a predetermined temperature generally corresponding to the desired sterilizing temperature. The temperature controller 48 is connected to the heater 24 through the control circuit 30 and is operable to produce an output signal when the gas temperature in the vicinity of the temperature sensor 46 is above the predetermined level or a set point. Other means, such as a conventional optical sensor, can be used to sense the presence of a relatively dense vapor blanket.

Once the instruments 36 have been completely enveloped with vapors 39, a blanket of the vapors rises above the tray 36 and contacts the temperature sensor 46. When the temperature of the vapors 39 contacting the temperature sensor 46 exceeds the set point of the temperature controller 48, the temperature controller produces an output signal which starts the sterilizing cycle.

The temperature controller 48 is also operable to fully energize the heater 24 in the event the temperature of the vapors 39 in the vicinity of the temperature sensor 46 drops below the set point during the sterilizing cycle. Thus, if the vapor blanket falls below the level of the temperature sensor 46 with a concomitant drop in the gas temperature, the temperature controller 48 energizes the heater 24 to produce additional hot vapors. As a consequence, a relatively stable blanket or zone of the vapors 39 is maintained over and above the instruments 36 to insure complete sterilization. The control circuit 30 includes a light emitting diode (LED) 50 or similar indicating means which is illuminated in response to the temperature controller 48 first responding to the presence of the vapor blanket at the level of the temperature sensor 46 and remains illuminated throughout the sterilizing cycle.

Means are provided for removing vapors of the sterilizing liquid 22 entrained in the air displaced from the chamber 14 and discharged through the vent passage 40. In the embodiment illustrated in FIGS. 1, 2 and 4, such means comprises a filter arrangement 60 including a L-shaped conduit 62 located inside the cover 16 with one end 64 connected in communication with the vent passage 40 and the opposite end 66 communicating with the atmosphere. The conduit 60 is packed with glass beads 68 and particulate charcoal 70 or other suitable medium for removing and/or condensing the vapors of the sterilizing liquid 22 from the air stream passing through the conduit 62.

The vapors of the sterilizing liquid 22 condense as the instruments 36, the tray 38 and the chamber 14 cool after the sterilizing cycle is completed as described in more detail below. The . resulting reduced pressure inside the chamber 14 causes a back flow of atmospheric air through the conduit 62. As this air passes through the charcoal 70 and the glass beads 68, the captured vapors and/or condensate are purged back into the chamber 14.

The control circuit 30 includes means for turning off or de-energizing the heater 24 after completion of the sterilizing cycle. Various suitable means, including conventional timing devices can be used for this purpose. In the embodiment illustrated, the control circuit 30 includes a conventional counting means 72 which is operable, in response to receiving an output signal from the temperature controller 48, to count the electrical energy cycles thereafter transmitted to the heater 24 and to terminate the flow of electrical energy to the heater 24 after a predetermined number of such cycles. The counting means 72 can be a conventional pulse clock generator which is operable to count the number of hertz (H₃) cycles transmitted to the heater 24 after receiving an output signal from the temperature controller 48 and to turn off the heater 24 after the predetermined number of cycles. Thus, a constant amount of electrical energy is transmitted to the heater 24 during the sterilizing cycle for each load to insure complete sterilization. If the building power supply decreases because of a large surge in usage, the counter 72 measures this and keeps the heater 24 on for a longer time to compensate for the reduction in energy level.

The control circuit 30 includes a light emitting diode (LED) 74 or other suitable indicating means which is illuminated in response to an output signal from the counting means 72 for de-energizing the heater 24 upon the completion of the sterilizing cycle.

With above-described control for maintaining the vapor blanket at a predetermined level, the vapors 39 do not completely fill the chamber 14 as illustrated in FIG. 2 and the internal pressure remains relatively low, close to atmospheric pressure and never as high as 15 p.s.i.g. Thus, the sterilizing device 10 does not have to be designed to withstand high internal pressures like most autoclave type sterilizers. Also, loss of vapors from the sterilizing liquid are minimized because only insubstantial amounts are expelled from the chamber 14 through the vent passage 40 and vapors entrained in the air stream discharged through the vent passage 40 are removed by the filter arrangement 60.

The control circuit 30 includes a coolant control 80 which is operable to energize an electrically-operated cooling means, such as fan 82 located in the rear of the housing 12, in response to the output signal from the counting means 72 for de-energizing the heater 24 upon completion of the sterilizing cycle. The fan 82 circulates air through the space 84 between the interior walls of the housing 12 and the exterior walls of the chamber 14 to promote cooling of the chamber 14 and condensation of the vapors. The housing 12 includes suitable air inlets and outlets (not shown) to afford free circulation of ambient air over the exterior walls of the chamber 14.

As the vapor level drops below the instruments 36, the latent heat thereof rapidly completely dries them so there is no residue. The interior walls of the chamber 14 preferably are arranged to promote drainage of condensed vapors collecting thereon back into the reservoir 20.

Other suitable cooling means can be used, such as a liquid coolant circulating through coils located inside the chamber 14 or encircling the exterior walls of the chamber 14 or a grid arrangement inside the chamber 14 for producing an electrostatic discharge to reduce the latent and sensible heat.

The coolant controller 80 is also operable to de-energize the fan 82 upon the occurrence of a predetermined event. In the specific embodiment illustrated, the control circuit 30 includes a temperature sensor 86 for sensing the gas temperature inside the chamber 14 and the coolant control 80 is operable to de-energize the fan 82 in response to the temperature sensor 86 detecting a temperature below a predetermined level or set point suitable for removing the instruments 36 without a significant amount of the vapors 39 escaping. Other suitable means can be used for controlling the operating time of the fan 82, such as a temperature controller having a temperature sensor which senses the temperature of the outer surface of the chamber 14 or a timer set for a predetermined time in the order of 10 to 15 minutes. The control circuit 30 includes a light emitting diode (LED) 88 or other suitable indicating means which is illuminated in response to the output signal from the coolant controller 80 for turning off the fan 82.

The various components of the control circuit 30 are illustrated schematically and shown external to the housing 12 for the sake of clarity. In actual practice, all the components, except the temperature sensors 46 and 86 (and the electrical source 28 if the device is arranged to be plugged into an electrical outlet), are housed in a control compartment 90 located on the front of the housing 12 and including a control panel 92 on which the various operating switches and illuminating indicators are mounted.

In operation, the instruments 36 are first cleaned with water and soap or ultrasonically and then placed in the tray 38. After the cover 16 is closed, the starter switch 32, which preferably is a momentary push button, is moved to the "on" position to start the sterilizing cycle. The heater 24 is energized to heat the liquid 22 to boiling and the indicator 34 is illuminated. The indicator 50 is illuminated when the temperature sensor 46 senses the presence of a vapor blanket above the instruments 36 and remains illuminated during the sterilizing cycle. The indicator 34 goes on and off as the heater 24 is energized and de-energized during the sterilizing cycle as the vapor blanket rises and falls below the temperature sensor 46 as described above. Both the indicators 34 and 50 go off and the indicator 74 is illuminated when the sterilizing cycle is completed as determined by the counting means 72. The indicator 88 is illuminated when the fan 82 is energized and both the indicator 74 and 88 go off when the fan 82 is de-energized by the coolant controller 80.

The cover 16 can be opened to remove the instruments 36 after the sterilizing cycle has been completed because there is little or no pressure build up inside the chamber 14. However, the cover 16 preferably is not opened until after the fan 82 has turned off in order to prevent the loss of vapors still present in the chamber 14.

FIG. 5 illustrates an alternate embodiment for the vapor recovery means. This embodiment includes a filter/condenser arrangement 100 including a generally U-shaped conduit or tube 102 having one end 104 connected in communication with the vent passage 40 and the other end 106 connected in communication with the atmosphere. The lower portion 108 of the tube 102 serves as a liquid trap for condensed vapors of the sterilizing liquid 22 removed from the air stream passing through the tube 102. Porous filters 110 and 112 are located in the tube 102 upstream and downstream of the liquid trap portion 108 and glass beads 114 and particulate charcoal 116 packed in the tube 102 downstream of the filter 112 serve to assist in removing and/or condensing vapors from the air steam, flowing through the tube 102 during the sterilizing cycle.

Atmospheric air flows back through the tube 102 after completion of the sterilizing cycle and the chamber 14 is cooled as described above. The sterilizing liquid 22 collected in the liquid trap 108 is returned to the chamber 14 through the vent passage 40 or directly to the reservoir 22 via a conduit 118 (fragmentarily illustrated by dashed lines) connected in fluid communication with the liquid trap portion 108 and the reservoir 20.

FIG. 6 illustrates another alternate embodiment for the vapor recovery means. This embodiment includes an inflatable and collapsable member or bladder 120 located in a chamber 122 defined inside the cover 16 and having an inlet 124 connected in communication with the vent passage 40. The bladder 120 has an inflatable volume large enough to collect all the air displaced from the chamber 114 by the vapor blanket during the sterilizing cycle. The cover chamber 122 is closed to the atmosphere and the bladder 120 is inflated as it receives the displaced air containing entrained vapors of the sterilizing liquid 22.

When the chamber 14 cools and the vapors therein start to condense after completion of the sterilizing cycle, the reduced pressure in the chamber 14 causes the air and vapors in the bladder 120 to flow back into the chamber 14 and the bladder 120 eventually collapses to a deflated condition. A one-way check valve 130 can be provided in the cover chamber 122 to insure a balanced pressure condition between the chamber 14 and the cover chamber 122.

I claim:

1. A sterilizing device comprising a housing having an openable access closure and defining an interior chamber having upper and lower portions,
   a reservoir means in the lower portion of said chamber containing a substantially non-toxic, substantially inert, vaporizable sterilizing liquid having a boiling point sufficiently high to kill microorganisms unsafe for humans,
   electrical heating means for heating and vaporizing the sterilizing liquid and providing a rising blanket of substantially saturated vapors of said sterilizing liquid,
   support means located above said reservoir means supporting articles to be sterilized and permitting the rising vapors to contact and pass over the articles,
   electrical control circuit means connected to a source of electrical energy and to said heating means for controlling the operation of said heating means and thereby controlling the level of the vapors in said chamber, said control circuit means including,
   means located above said support means and the articles supported thereon for sensing the presence and absence of a relatively dense blanket of the vapors,
   means electrically interconnecting said sensing means and said heating means for permitting the flow of electrical energy to said heating means in response to said sensing means sensing the absence of a vapor blanket and for terminating the flow of electrical energy to said heating means after a predetermined period sufficient to sterilize the articles subsequent to said sensing means sensing the presence of a vapor blanket, and
   vent passage means providing an opening to the atmosphere throughout normal operation of said device for discharging to the atmosphere the air displaced from said chamber by the rising vapor blanket, said vent passage means including an inlet communicating with said chamber at a location above said sensing means and an outlet communicating with the atmosphere.

2. A sterilizing device according to claim 1 including means in said vent passage means for recovering vapors of the sterilizing liquid entrained in an air stream passing said through vent passage means.

3. A sterilizing device according to claim 2 wherein said vapor recovery means is constructed so that condensed vapors are returned to said reservoir means by a backflow of atmospheric air through said vent passage means in response to said chamber cooling after completion of a sterilizing cycle.

4. A sterilizing device according to claim 3 wherein said vent passage means includes a conduit which is generally U-shaped to form a liquid trap for the condensed vapors and said means for recovering vapors includes a porous medium for removing vapors of the sterilizing liquid in the air stream passing therethrough.

5. A sterilizing device according to claim 1 wherein said heating mean is submerged in and is in direct contact with the sterilizing liquid.

6. A sterilizing device according to claim 5 wherein said heating means includes a heating element comprising a positive temperature coefficient thermistor material which produces a substantially constant surface temperature irrespective of variations in electrical energy supplied thereto.

7. A sterilizing device according to claim 6 wherein said vapor sensing means comprises a temperature sensing means.

8. A sterilizing device according to claim 1 wherein said control circuit means includes counter means for counting the number of cycles of electrical energy transmitted to said heating means after said sensing means senses the presence of a vapor blanket and for terminating the flow of electrical energy to said heating means after a predetermined number of such cycles.

9. A sterilizing device according to claim 1 including an electrically-operated cooling means and wherein said control circuit means includes means for energizing said cooling means in response to the termination of the flow of electrical energy to said heating means upon completion of a sterilizing cycle.

10. A method for sterilizing articles such as surgical instruments, dental instruments and the like including the steps of
   providing a chamber having a cover, an upper portion and a lower portion including a reservoir containing a substantially non-toxic, substantially inert, vaporizable sterilizing liquid having a boiling point sufficiently high to kill microorganisms unsafe for humans and further including a vent passage having an inlet communicating with the upper portion of the chamber and an outlet communicating with the atmosphere throughout sterilization,
   positioning the articles to be sterilized in the chamber at a location above the reservoir,
   heating and vaporizing the sterilizing liquid to provide a rising blanket of substantially saturated vapors of the sterilizing liquid which contacts and passes over the articles to be sterilized and displaces air from the chamber to the atmosphere through the vent passage,
   detecting the presence and absence of a relatively dense blanket of said vapors in the chamber at a location above the articles to be sterilized and below the inlet of the vent passage,
   after detecting the presence of said vapor blanket at said location, continuing heating of the sterilizing liquid for a predetermined period to provide sufficient exposure of the articles to said vapors for sterilization; and
   terminating heating of the sterilizing liquid after said period.

11. A method according to claim 10 wherein said sterilizing liquid is a fluorocarbon liquid having a boiling point of at least about 100° C.

12. A method according to claim 11 wherein said fluorocarbon liquid has a boiling point of at least about 150° C.

* * * * *